(12) United States Patent
Vazquez

(10) Patent No.: US 8,096,955 B1
(45) Date of Patent: Jan. 17, 2012

(54) SPECIMEN COLLECTION SYSTEM

(76) Inventor: Theresa P. Vazquez, East Orange, NJ (US)

( * ) Notice: Subject to any disclaimer, the term of this patent is extended or adjusted under 35 U.S.C. 154(b) by 457 days.

(21) Appl. No.: 12/174,176

(22) Filed: Jul. 16, 2008

(51) Int. Cl.
*A61B 5/00* (2006.01)
*A61B 10/00* (2006.01)
*B65D 81/00* (2006.01)

(52) U.S. Cl. ........................................ 600/562; 600/573

(58) Field of Classification Search .......... 600/562–584; 604/317, 322, 324, 326, 327, 328, 332, 346, 604/347, 348, 356, 387; 119/850, 161, 162, 119/165, 166; 4/300, 300.1–300.3
See application file for complete search history.

(56) References Cited

U.S. PATENT DOCUMENTS

| | | | |
|---|---|---|---|
| 216,346 A * | 6/1879 | Read | 220/771 |
| 2,185,897 A * | 1/1940 | Krause et al. | 210/244 |
| 2,579,258 A * | 12/1951 | Heckert | 99/349 |
| 3,501,781 A * | 3/1970 | Ott | 4/483 |
| 4,276,889 A | 7/1981 | Kuntz et al. | |
| D267,273 S | 12/1982 | Paulin | |
| 4,961,431 A * | 10/1990 | Ikenaga et al. | 600/573 |
| 5,149,506 A * | 9/1992 | Skiba et al. | 422/557 |
| 5,337,426 A | 8/1994 | Matusewicz et al. | |
| 5,388,732 A * | 2/1995 | Greger | 222/572 |
| 5,422,076 A * | 6/1995 | Jones | 600/574 |
| 5,913,832 A | 6/1999 | Sagalovich et al. | |
| 5,967,024 A * | 10/1999 | DeMars | 99/425 |
| 6,151,972 A | 11/2000 | Venter et al. | |
| 6,602,231 B1 * | 8/2003 | Mariea | 604/317 |

* cited by examiner

*Primary Examiner* — Jeffrey G Hoekstra

(57) ABSTRACT

A specimen collection system for collecting urine and fecal samples for a person so that the urine and fecal samples can be tested includes a dish being positionable under a pelvis of a person to receive excretions from the person. The dish includes a bottom wall and a peripheral wall attached to and extending upwardly from the bottom wall. The peripheral wall has at least one pour spout formed therein and extending outwardly from a top edge of the peripheral wall to facilitate pouring of the excretions from the dish. A cover is positionable over the top edge of the dish and inhibits the excretions inadvertently spilling over the top edge of the dish when the cover is positioned over the top edge. At least one cup receives the excretions poured from the dish. The at least one cup stores the excretions for transport to be tested.

20 Claims, 5 Drawing Sheets

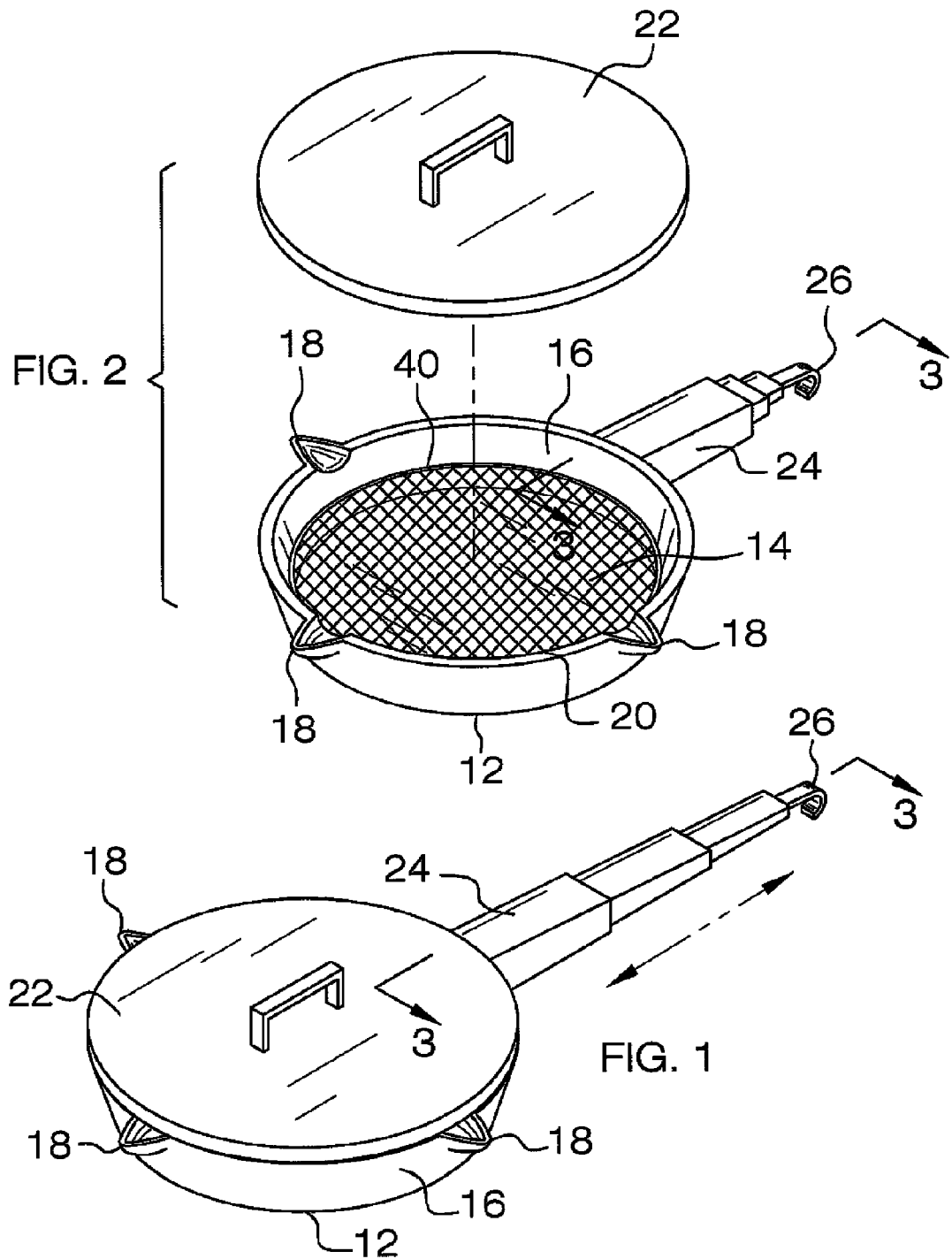

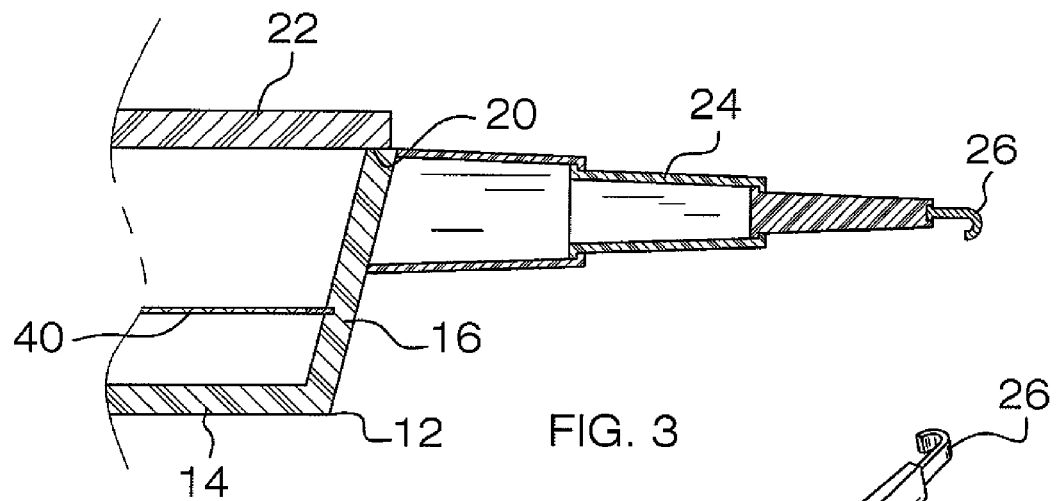
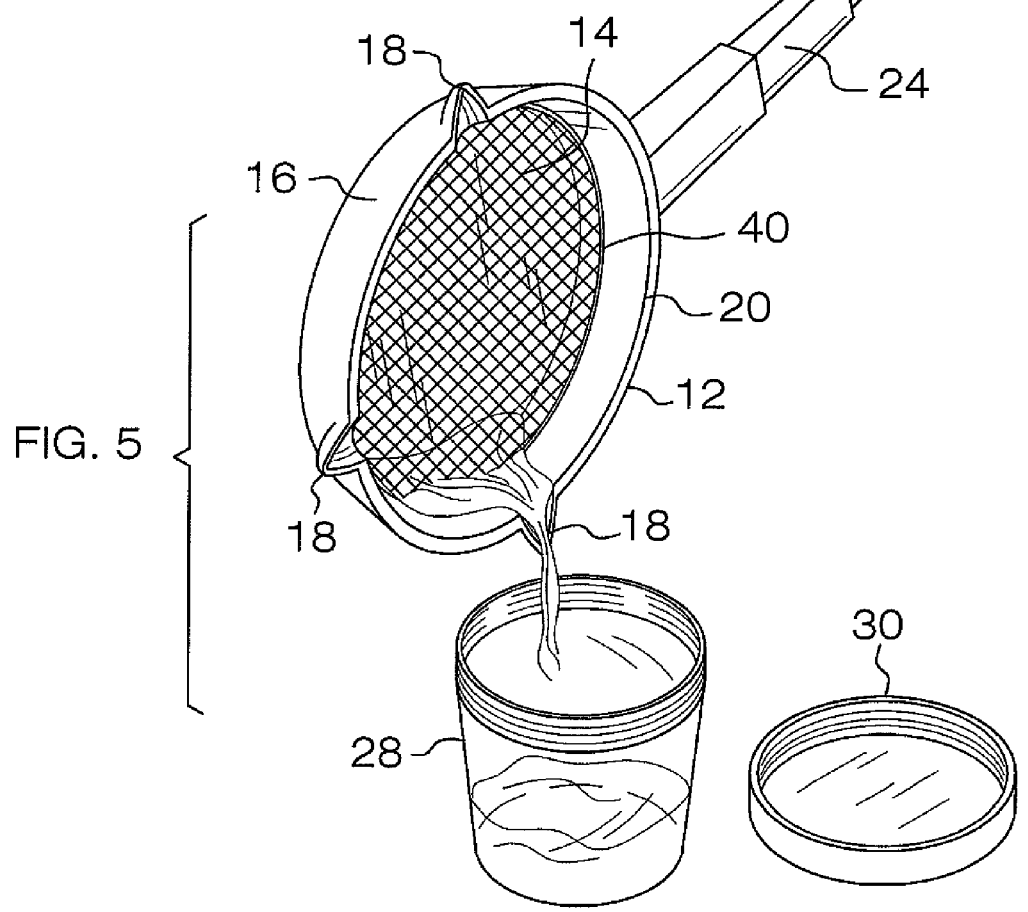

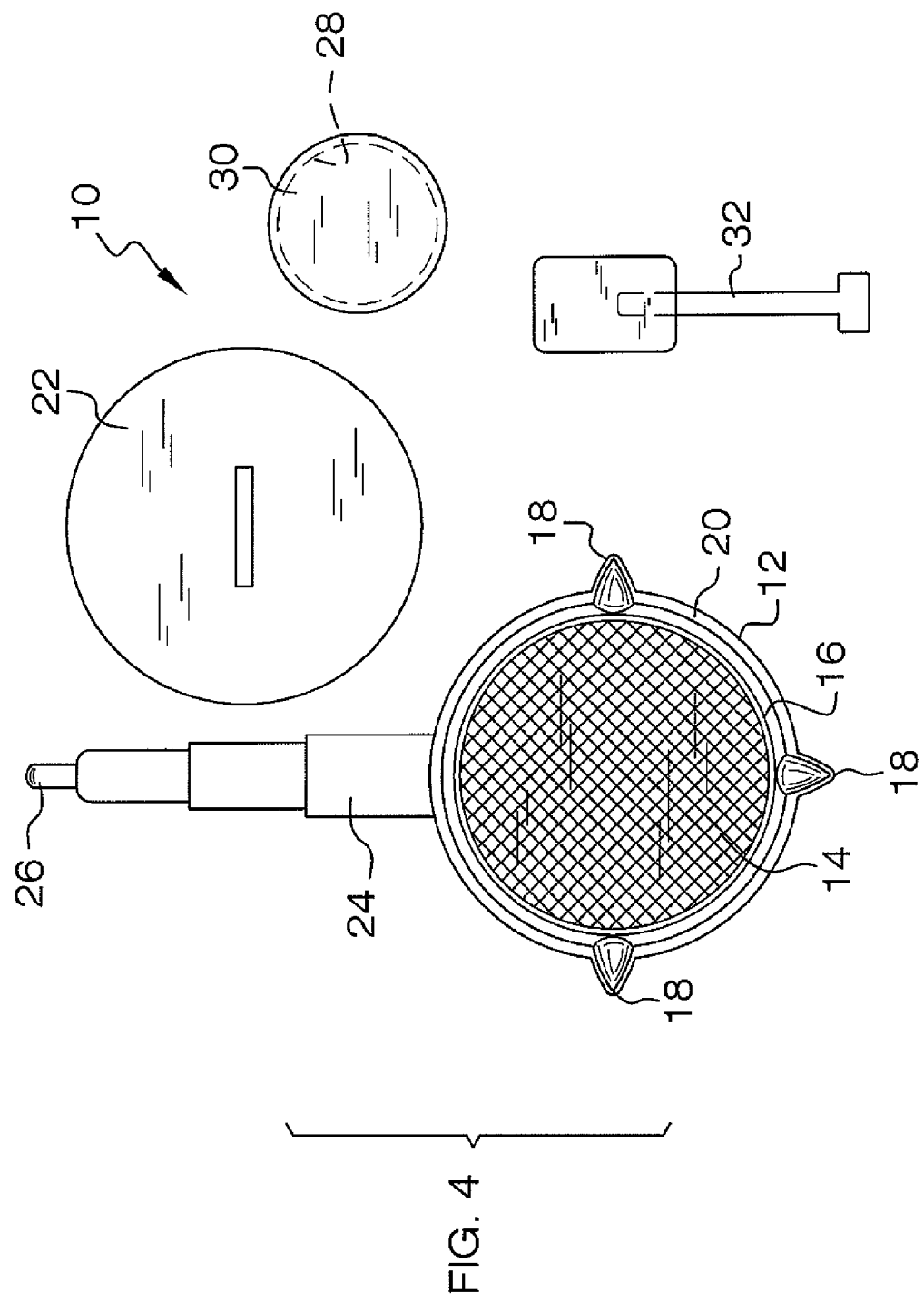

SPECIMEN COLLECTION SYSTEM

BACKGROUND OF THE INVENTION

1. Field of the Invention

The present invention relates to urine collection trays and more particularly pertains to a new urine collection tray for collecting urine and fecal samples for a person so that the urine and fecal samples can be tested.

2. Description of the Prior Art

The use of urine collection trays is known in the prior art. While these devices fulfill their respective, particular objectives and requirements, the need remains for a system that has certain improved features that allows for the system to be readily positioned under a pelvis of a person during urination or defecation to collect urine and fecal samples. Additionally, the system should include a telescopic handle to provide a greater flexibility in positioning the system for collecting the samples.

SUMMARY OF THE INVENTION

The present invention meets the needs presented above by generally comprising a dish being positionable under a pelvis of a person to receive excretions from the person. The dish includes a bottom wall and a peripheral wall attached to and extending upwardly from the bottom wall. The peripheral wall has at least one pour spout formed therein and extending outwardly from a top edge of the peripheral wall. The at least one pour spout extends from the top edge toward the bottom wall. The at least one pour spout facilitates pouring of the excretions from the dish. A cover is positionable over the top edge of the dish. The cover inhibits the excretions inadvertently spilling over the top edge of the dish when the cover is positioned over the top edge. At least one cup receives the excretions poured from the dish. The at least one cup stores the excretions for transport to be tested.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a dish and cover of a specimen collection system according to the present invention.

FIG. 2 is a perspective view of the dish and cover of the present invention.

FIG. 3 is a cross-sectional view of the present invention taken along line 3-3 of FIG. 2.

FIG. 4 is a top view of the present invention.

FIG. 5 is a perspective view of the present invention showing excretion collected in the dish being poured into a cup.

DESCRIPTION OF THE PREFERRED EMBODIMENT

Figure 6:
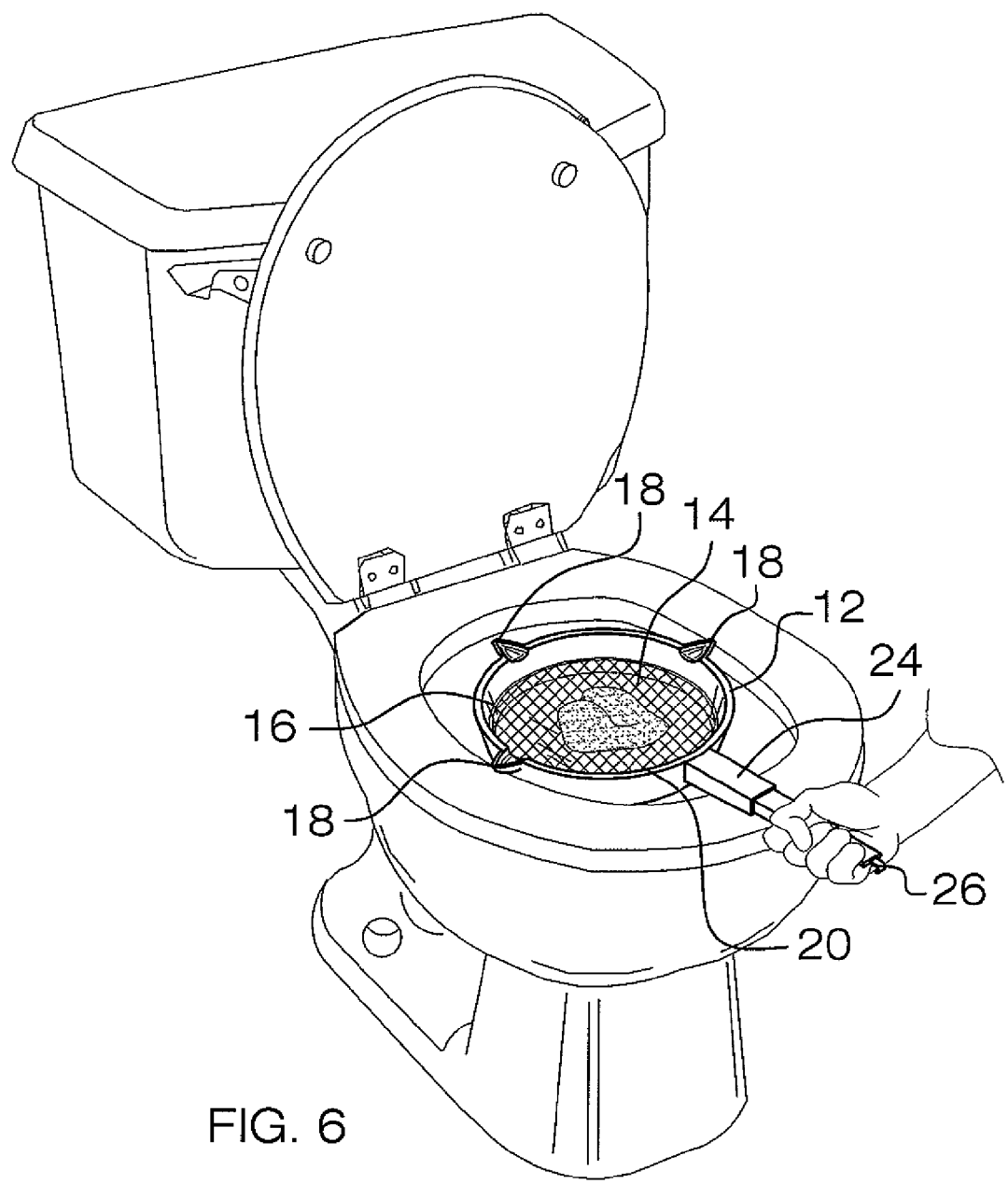
FIG. 6 is a perspective view of the dish of the present invention positioned over a toilet to collect a fecal sample.

With reference now to the drawings, and in particular to FIGS. 1 through 7 thereof, a new urine collection tray embodying the principles and concepts of the present invention and generally designated by the reference numeral 10 will be described.

As best illustrated in FIGS. 1 through 7, the specimen collection system 10 generally comprises a dish 12 being positionable under a pelvis of a person to receive excretions from the person. The dish 12 includes a bottom wall 14 and a peripheral wall 16 attached to and extending upwardly from the bottom wall 14. The peripheral wall 16 has at least one pour spout 18 formed therein and extending outwardly from a top edge 20 of the peripheral wall 16. The at least one pour spout 18 extends from the top edge 20 toward the bottom wall 14. The at least one pour spout 18 facilitates pouring of the excretions from the dish 12. The at least one pour spout 18 includes three pour spouts 18. Two of the pour spouts 18 are positioned opposite of each other and equally spaced from a third one of the pour spouts 18.

A cover 22 is positionable over the top edge 20 of the dish 12. The cover 22 inhibits the excretions inadvertently spilling over the top edge 20 of the dish 12 when the cover 22 is positioned over the top edge 20. The cover 22 has a same size and shape as the top edge 20. The cover 22 allows fluids to be poured outward through one of the pour spouts 18 when the cover 22 is abutted against the top edge 20.

Figure 7:
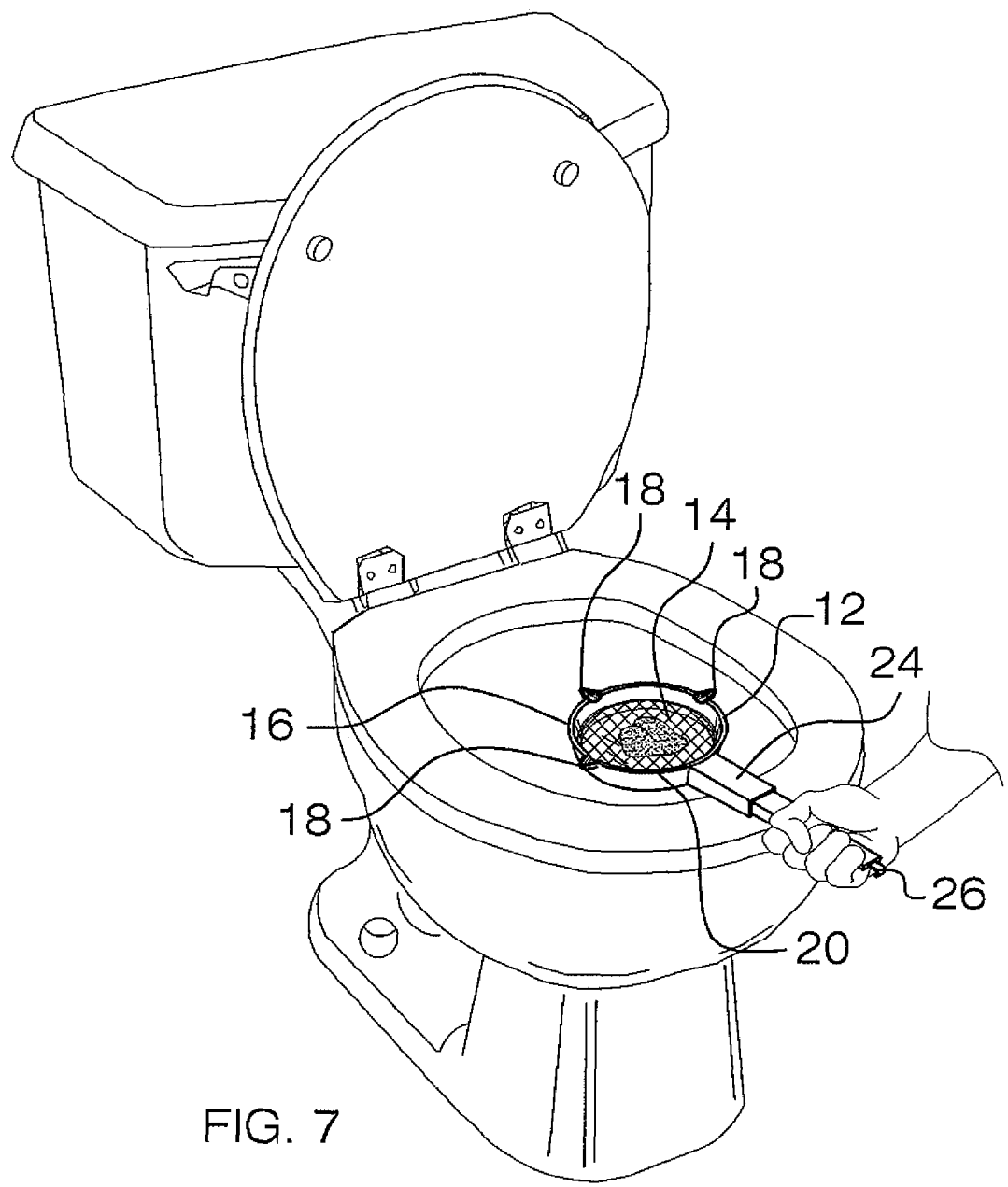
FIG. 7 is a perspective view of the dish of the present invention positioned over a toilet to collect a fecal sample.

A handle 24 is coupled to the dish 12. The handle 24 is graspable to facilitate manipulation of the dish 12. The handle 24 is telescopic to permit changing of a length of the handle 24. The handle 24 includes a free end 26. The free end 26 is hook shaped to facilitate hanging of the dish 12 when the dish 12 is not being used. The third one of the pour spouts 18 is positioned opposite of the handle 24. As shown in FIG. 6, a portion of the pour spouts 18 can be positioned on the seat of a toilet to help support the dish 12 under the pelvis of the person when the person can not easily hold the handle 24 to maintain the position of the dish 12. In FIG. 7, a smaller version of the dish 12 is used and the pour spouts 18 do not rest on the seat of the toilet when the person can hold the handle 24 and maintain position of the dish 12.

At least one cup 28 receives the excretions poured from the dish 12. The at least one cup 28 store the excretions for transport to be tested. At least one lid 30 is threadably mountable to the at least one cup 28. The at least one lid 30 closes the at least one cup 28 to inhibit the excretions spilling when the at least one lid 30 is mounted to the at least one cup 28. A spatula 32 is graspable to facilitate manipulation of the spatula 32. The spatula 32 is wiped against the dish 12 to maximize the amount of excretions transferred from the dish 12 to the at least one cup 28.

A screen 40 is mounted in the dish 12 and oriented parallel to the bottom wall 14. The screen 40 is spaced from the top edge 20 and helps to retain solid matter from fluidic matter.

In use, the dish 12 is positioned under the pelvis of the person as the person is urinating to collect the urine. The dish 12 is removed and the urine is poured into the at least one cup 28 and the lid 30 is positioned on the cup 28 to secure the urine in the at least one cup 28. To collect a fecal sample the dish 12 is positioned under the pelvis of the person while the person is defecating and the feces is collected in the dish 12. The spatula 32 is then used to scrape the feces into the at least one cup 28. The lid 30 is secured to the at least one cup 28 to secure the feces within the cup 28. FIGS. 6 and 7 show different sizes of dishes 12 to be used depending on the condition of the person who is providing the sample and the type of toilet being used.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A specimen collection system for collecting excreted samples from a person, said system comprising:
    a dish being positionable under a pelvis of a person to receive excretions from the person, said dish including a bottom wall and a peripheral wall being attached to and extending upwardly from said bottom wall, said peripheral wall having three pour spouts formed therein and extending outwardly from a top edge of said peripheral wall, said each of said pour spouts extending from said top edge toward said bottom wall, said pour spouts facilitating pouring of the excretions from said dish;
    a cover being positionable over said top edge of said dish, said cover inhibiting the excretions inadvertently spilling over said top edge of said dish when said cover is positioned over said top edge; and
    at least one cup receiving the excretions poured from said dish, said at least one cup storing the excretions for transport to be tested.

2. The system according to claim 1, wherein two of said pour spouts are positioned opposite of each other and equally spaced from a third one of said pour spouts.

3. The system according to claim 1, wherein said cover has a same size and shape as said top edge, said cover allowing fluids to be poured outward through one of said pour spouts when said cover is abutted against said top edge.

4. The system according to claim 1, further comprising a handle being coupled to said dish, said handle being graspable to facilitate manipulation of said dish.

5. The system according to claim 4, wherein said handle being telescopic to permit changing of a length of said handle.

6. The system according to claim 4, wherein said handle includes a free end, said free end being hook shaped to facilitate hanging of said dish when said dish is not being used.

7. The system according to claim 1, further comprising at least one lid being threadably mountable to said at least one cup, said at least one lid closing said at least one cup to inhibit the excretions spilling when said at least one lid is mounted to said at least one cup.

8. The system according to claim 1, further comprising a spatula being graspable to facilitate manipulation of said spatula, said spatula being wiped against said dish to maximize the amount of excretions transferred from said dish to said at least one cup.

9. A specimen collection system for collecting excreted samples from a person, said system comprising:
    a dish being positionable under a pelvis of a person to receive excretions from the person, said dish including a bottom wall and a peripheral wall being attached to and extending upwardly from said bottom wall, said peripheral wall having at least one pour spout formed therein and extending outwardly from a top edge of said peripheral wall, said at least one pour spout extending from said top edge toward said bottom wall, said at least one pour spout facilitating pouring of the excretions from said dish, said at least one pour spout including three pour spouts, two of said pour spouts being positioned opposite of each other and equally spaced from a third one of said pour spouts;
    a cover being positionable over said top edge of said dish, said cover inhibiting the excretions inadvertently spilling over said top edge of said dish when said cover is positioned over said top edge, said cover having a same size and shape as said top edge, said cover allowing fluids to be poured outward through one of said pour spouts when said cover is abutted against said top edge;
    a handle being coupled to said dish, said handle being graspable to facilitate manipulation of said dish, said handle being telescopic to permit changing of a length of said handle, said handle including a free end, said free end being hook shaped to facilitate hanging of said dish when said dish is not being used, said third one of said pour spouts being positioned opposite of said handle;
    at least one cup receiving the excretions poured from said dish, said at least one cup storing the excretions for transport to be tested;
    at least one lid being threadably mountable to said at least one cup, said at least one lid closing said at least one cup to inhibit the excretions spilling when said at least one lid is mounted to said at least one cup; and
    a spatula being graspable to facilitate manipulation of said spatula, said spatula being wiped against said dish to maximize the amount of excretions transferred from said dish to said at least one cup.

10. The system according to claim 9, further including a screen being mounted in said dish and attached to said peripheral wall, said screen covering and being spaced from said bottom wall, said screen being oriented parallel to said bottom wall.

11. The system according to claim 1, wherein said bottom wall is solid such that fluid is pourable out of said dish only over an upper edge of said peripheral wall or outwardly of said at least one pour spout.

12. The system according to claim 9, wherein said bottom wall is solid such that fluid is pourable out of said dish only over an upper edge of said peripheral wall or outwardly of said pour spouts.

13. The system according to claim 10, wherein said bottom wall is solid such that fluid is pourable out of said dish only over an upper edge of said peripheral wall or outwardly of said at least one pour spout.

14. A specimen collection system for collecting excreted samples from a person, said system comprising:
    a dish being positionable under a pelvis of a person to receive excretions from the person, said dish including a bottom wall and a peripheral wall being attached to and extending upwardly from said bottom wall, said peripheral wall having at least one pour spout formed therein and extending outwardly from a top edge of said peripheral wall, said at least one pour spout extends from said top edge toward said bottom wall, said at least one pour spout facilitating pouring of the excretions from said dish;
- a cover being positionable over said top edge of said dish, said cover inhibiting the excretions inadvertently spilling over said top edge of said dish when said cover is positioned over said top edge;
- at least one cup receiving the excretions poured from said dish, said at least one cup storing the excretions for transport to be tested; and
- a screen being mounted in said dish and attached to said peripheral wall, said screen covering and being spaced from said bottom wall, said screen being oriented parallel to said bottom wall.

15. The system according to claim 14, wherein said at least one spout includes a pair of pour spouts positioned opposite of each other.

16. The system according to claim 14, wherein said cover has a same size and shape as said top edge, said cover allowing fluids to be poured outward through one of said pour spouts when said cover is abutted against said top edge.

17. The system according to claim 14, further comprising a handle being coupled to said dish, said handle being graspable to facilitate manipulation of said dish.

18. The system according to claim 17, wherein said handle being telescopic to permit changing of a length of said handle.

19. The system according to claim 17, wherein said handle includes a free end, said free end being hook shaped to facilitate hanging of said dish when said dish is not being used.

20. The system according to claim 14, further comprising at least one lid being threadably mountable to said at least one cup, said at least one lid closing said at least one cup to inhibit the excretions spilling when said at least one lid is mounted to said at least one cup.

\* \* \* \* \*